(12) United States Patent
Zur et al.

(10) Patent No.: US 11,921,182 B2
(45) Date of Patent: Mar. 5, 2024

(54) ACCELERATED MAGNETIC RESONANCE THERMOMETRY

(71) Applicant: INSIGHTEC, LTD., Tirat Carmel (IL)

(72) Inventors: Yuval Zur, Tirat Carmel (IL); Boaz Shapira, Tirat Carmel (IL); Yoav Levy, Hinanit (IL)

(73) Assignee: INSIGHTEC LTD., Tirat Carmel (IL)

( * ) Notice: Subject to any disclaimer, the term of this patent is extended or adjusted under 35 U.S.C. 154(b) by 117 days.

(21) Appl. No.: 17/604,835

(22) PCT Filed: Apr. 21, 2020

(86) PCT No.: PCT/IB2020/000294
§ 371 (c)(1),
(2) Date: Oct. 19, 2021

(87) PCT Pub. No.: WO2020/217098
PCT Pub. Date: Oct. 29, 2020

(65) Prior Publication Data
US 2022/0196771 A1 Jun. 23, 2022

Related U.S. Application Data

(60) Provisional application No. 62/838,409, filed on Apr. 25, 2019, provisional application No. 62/931,525, filed on Nov. 6, 2019, provisional application No. 62/971,449, filed on Feb. 7, 2020.

(51) Int. Cl.
*G01V 3/00* (2006.01)
*A61B 5/055* (2006.01)
(Continued)

(52) U.S. Cl.
CPC .......... *G01R 33/5608* (2013.01); *A61B 5/055* (2013.01); *G01R 33/4818* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

2002/0107858 A1* 8/2002 Lundahl .................. G06F 18/23
2011/0178386 A1* 7/2011 Grissom ............ G01R 33/4804
600/410

(Continued)

FOREIGN PATENT DOCUMENTS

CN 1515912 A * 7/2004
CN 106250707 A * 12/2016 ........... G06F 19/321
WO WO-2017004482 A1 * 1/2017 ............. A61B 18/24

OTHER PUBLICATIONS

PCT International Patent Application No. PCT/IB2020/000294, International Search Report and Written Opinion mailed Oct. 27, 2020, 28 pages.

(Continued)

*Primary Examiner* — Walter L Lindsay, Jr.
*Assistant Examiner* — Frederick Wenderoth
(74) *Attorney, Agent, or Firm* — MORGAN, LEWIS & BOCKIUS LLP

(57) ABSTRACT

Systems and methods provide accelerated MR thermometry utilizing prior knowledge about the images to be reconstructed from incomplete k-space data, thereby facilitating accurate reconstruction. In various embodiments, missing data is computationally estimated using a machine learning algorithm such as a neural network, and an image is generated based on iteratively updated estimated missing information.

28 Claims, 10 Drawing Sheets

(51) Int. Cl.
*G01R 33/48* (2006.01)
*G01R 33/50* (2006.01)
*G01R 33/56* (2006.01)
*G01R 33/561* (2006.01)
*G06N 3/08* (2023.01)

(52) U.S. Cl.
CPC .......... *G01R 33/50* (2013.01); *G01R 33/5611* (2013.01); *G01R 33/5615* (2013.01); *G06N 3/08* (2013.01)

(58) Field of Classification Search
USPC ........................................................ 324/309
See application file for complete search history.

(56) References Cited

U.S. PATENT DOCUMENTS

| 2012/0068703 | A1  | 3/2012  | Gross et al. |
| 2012/0257806 | A1  | 10/2012 | Sheltraw et al. |
| 2018/0092569 | A1* | 4/2018  | Li .......................... A61B 5/055 |

OTHER PUBLICATIONS

Yuan et al. "Towards fast and accurate temperature mapping with proton resonance frequency-based MR thermometry," 2012. Quantitative Imaging in Medicine and Surgery, vol. 2, No. 1, pp. 21-23 (Year: 2012).

Odeen, et al. "Dynamic anti-aliasing image reconstruction for localized thermal therapies," 2017. Journal of Magnetic Resonance in Medicine, vol. 25 (Year: 2017).

Dedmari, et al. "Complex Fully Convolutional Neural Networks for MR Image Reconstruction," 2018. arXiv e-prints, pp. 1-9 (Year: 2018) (Bibcode: arXiv:1807.03343).

Kim, et al. "Real-time interactive magentic resonance (MR) temperature imaging in both aqueous and adipose tissues using cascaded deep neural networks for MR-guided focused ultrasound surgery (MRgFUS)," 2019. pp. 1-36 (Year: 2019).

Han, et al. "K-Space Deep Learning for Accelerated MRI," 2019. arXiv e-prints, pp. 1-11 (Year: 2019) (Bibcode: arXiv:1805.03779v3).

Zimmerman, et al. "Accelerated Parameter Mapping of Multiple-Echo Gradient-Echo Data Using Model-Based Iterative Reconstruction," 2018. IEEE Transactions on Medical Imaging, vol. 37, No. 2, pp. 626-637 (Year: 2018).

Liu, et al. "Susceptibility-Weighted Imaging and Quantitative Susceptibility Mapping in the Brain," 2015. Journal of Magnetic Resonance Imaging, vol. 42, pp. 23-41 (Year: 2015).

Lundervold, et al. "An overview of deep learning in medical imaging focusing on MRI," 2018. arXiv e-prints, pp. 1-44 (Year: 2018) (Bibcode: 2018arXiv181110052S ).

* cited by examiner

ACCELERATED MAGNETIC RESONANCE THERMOMETRY

CROSS-REFERENCE TO RELATED APPLICATIONS

This application is the U.S. national stage application of International (PCT) Patent Application Serial No. PCT/IB32020/000294, filed Apr. 21, 2020, which claims priority to and the benefits of U.S. Provisional Application No. 62/838,409, filed on Apr. 25, 2019; 62/931,525, filed on Nov. 6, 2019; and 62/971,449, filed on Feb. 7, 2020. The entire disclosures of all of the foregoing documents are hereby incorporated by reference.

TECHNICAL FIELD

The present invention relates, in general, to magnetic resonance (MR) thermometry, and, in particular, to approaches for accelerating MR thermometry.

BACKGROUND

Tissue, such as a benign or malignant tumor or blood clot within a patient's skull or other body region, may be treated invasively by surgically removing the tissue or non-invasively by using, for example, thermal ablation. Both approaches may effectively treat certain localized conditions within the body, but involve delicate procedures to avoid destroying or damaging otherwise healthy tissue. Unless the healthy tissue can be spared or its destruction is unlikely to adversely affect physiological function, surgery may not be appropriate for conditions in which diseased tissue is integrated within healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to the relatively short wavelengths (e.g., as small as 1.5 millimeters (mm) in cross-section at one Megahertz (1 MHz)) of ultrasound. Moreover, because acoustic energy generally penetrates well through soft tissues, intervening anatomy often does not impose an obstacle to defining a desired focal zone. Thus, ultrasonic energy may be focused at a small target in order to ablate diseased tissue without significantly damaging surrounding healthy tissue.

An ultrasound focusing system generally utilizes an acoustic transducer surface, or an array of transducer surfaces, to generate an ultrasound beam. The transducer may be geometrically shaped and positioned to focus the ultrasonic energy at a "focal zone" corresponding to the target tissue mass within the patient. During wave propagation through the tissue, a portion of the ultrasound energy is absorbed, leading to increased temperature and, eventually, to cellular necrosis—preferably at the target tissue mass in the focal zone. The individual surfaces, or "elements," of the transducer array are typically individually controllable, i.e., their phases and/or amplitudes can be set independently of one another (e.g., using a "beamformer" with suitable delay or phase shift in the case of continuous waves and amplifier circuitry for the elements), allowing the beam to be steered in a desired direction and focused at a desired distance, and the focal zone properties to be shaped as needed. Thus, the focal zone can be rapidly displaced and/or reshaped by independently adjusting the amplitudes and phases of the electrical signal input into the transducer elements.

However, because the human body is flexible and moves even when a patient is positioned to keep still (due to respiration, for example, or small involuntary movements), treatment delivered as multiple sonications over time—even when sonications are delivered within seconds of each other—may require interim adjustments to targeting and/or to one or more treatment parameters. Compensation for motion is thus necessary to ensure that the ultrasound beam remains focused on the target and does not damage the surrounding healthy tissues.

Accordingly, an imaging modality, such as magnetic resonance imaging (MRI), may be used in conjunction with ultrasound focusing during non-invasive therapy to monitor the locations of both the target tissue and the ultrasound focus. Generally, an MRI system 100, as depicted in FIG. 1, includes a static-field magnet 102, one or more gradient-field coils 104, a radio-frequency (RF) transmitter 106, and an RF receiver (not shown). (In some embodiments, the same device is used alternately as RF transmitter or receiver.) The magnet includes a region 108 for receiving a patient 110 therein, and provides a static, relatively homogeneous magnetic field over the patient. Time-variable magnetic field gradients generated by the gradient-field coils 104 are superposed with the static magnetic field. The RF transmitter 106 transmits RF pulse sequences over the patient 110 to cause the patient's tissues to emit a (time-varying) RF response signal, which is integrated over the entire (two- or three-dimensional) imaging region and sampled by the RF receiver to produce a time series of response signals that constitute the raw image data. This raw data is passed on to a computation unit 112. Each data point in the time series can be interpreted as the value of the Fourier transform of the position-dependent local magnetization at a particular point in k-space (i.e., wavevector space), where the wavevector k is a function of the time development of the gradient fields. Thus, by inverse Fourier-transforming the time series of the response signal, the computation unit 112 can reconstruct an image of the tissue (i.e., an image showing the measured magnetization-affecting tissue properties as a function of spatial coordinates) from the raw data. The magnetic-resonance (MR) image may then be displayed to the user. The MRI system 100 may be used to plan a medical procedure, as well as to monitor treatment progress during the procedure. For example, MRI may be used to image an anatomical region, locate the target tissue (e.g., a tumor) within the region, guide the beam generated by the ultrasound transducer 114 to the target tissue, and/or monitor the temperature in and surrounding the target tissue.

While MM enables the advantageous use of image-guided systems, such as MRI-guided focused-ultrasound (MRgFUS) systems, in a variety of different treatment scenarios, in many cases the imaging rate (i.e., the rate at which successive MRI images may be acquired) lags behind the rate at which one or more characteristics of the target change. For example, during a focused ultrasound treatment or other exposure to therapeutic energy, the location or temperature of the target may rapidly change, resulting in large discontinuous jumps from one full MRI scan to another. This inability to track changes in the target at a sufficiently fine timescale may result in significant inefficiencies in the treatment process (as it may be necessary to stop and reset the treatment to account for the change) or even dangerous exposure to treatment energy of the target or to untargeted tissue.

One conventional approach to counter this problem accelerates the MR imaging rate by acquiring only partial raw k-space data during scanning (i.e., "under-sampling" the k-space data); an algorithm involving a cost function may then be iteratively performed to generate an image using the under-sampled k-space data. The cost function generally includes a data fidelity term, which ensures faithfulness to the originally acquired sparse data, and a constraint term that may be realized as a model that maximizes smoothness of the data over time. Although reducing the acquisition of k-space data points may increase the MR imaging rate, the process for complementing information about the "missing" (or non-acquired) k-space data during the imaging reconstruction process may be time consuming due to lack of prior knowledge about the images to be reconstructed; as a result, the increased MR imaging rate is compromised. Generally, the more prior knowledge that is obtained, the less sampled k-space data is required, which can then achieve a larger acceleration of the MR imaging rate. Accordingly, there is a need for an improved MRI acquisition approach that implements additional prior knowledge about the images to be reconstructed, thereby further reducing the amount of k-space data required during MR scanning for image reconstruction as well as further accelerating the MR imaging rate.

SUMMARY

Embodiments of the present invention provide accelerated MR thermometry utilizing prior knowledge about the images to be reconstructed from incomplete k-space data, thereby facilitating accurate reconstruction. In various embodiments, missing data is computationally estimated using a machine learning algorithm such as a neural network, and an image is generated based on iteratively updated estimated missing information.

Accordingly, in one aspect, the invention pertains to an imaging system comprising, in various embodiments, an MRI apparatus configured to excite a target region. The target region may include, consist essentially of, or consist of a feature (e.g., an anatomical feature of a human or animal, a treatment target, a non-treatment target, a phantom such as an imaging phantom, etc.). In various embodiments, the MRI apparatus is configured to (i) execute a first multi-echo pulse sequence to excite a target region; (ii) acquire a plurality of baseline k-space images of the target region, each baseline image being associated with an echo in the first multi-echo pulse sequence; (iii) execute a second multi-echo pulse sequence to excite the target region; and (iv) acquire a second plurality of k-space images. Each of the second plurality of k-space images may be associated with an echo in the second multi-echo pulse sequence and at least one of the second plurality of k-space images may be under-sampled so as to be missing information compared to the baseline k-space images. In some embodiments, all of the second plurality of k-space images are under-sampled. In one embodiment, at least one of the second plurality of k-space images is under-sampled in a different pattern. In addition, the image system may include a computation unit configured to reconstruct a target image based at least in part on at least one baseline k-space image and at least one of the second plurality of k-space images.

In some embodiments, the computation unit comprises or executes a machine-learning algorithm such as a neural network, e.g., a convolutional neural network. The target image may be a thermal map, a susceptibility-weighted image, a $T_2^*$ image, a micro-bleeding image or a BOLD f-MRI image.

In various embodiments, the system is configured such that, for at least one of the second plurality of k-space images, the missing information is computationally estimated using the neural network, and a target image is generated based at least in part on the updated estimated missing information. The computation unit may be configured to, for at least one of the second plurality of k-space images, (i) computationally estimate the corresponding anatomical image using the neural network, and (ii) generate a target image based at least in part on the updated estimated anatomical image. Alternatively or in addition, the computation unit may be configured to, for at least one of the second plurality of k-space images, (i) estimate the information missing therefrom and reconstruct a corresponding anatomical image, (ii) computationally correct anatomical image using the neural network, and (ii) generate a target image based at least in part on the updated estimated anatomical image. In still another alternative, the computation unit is configured to, for at least one of the second plurality of k-space images, (i) computationally estimate the information missing therefrom, (ii) computationally update the estimated missing information based at least in part on an echo time associated therewith, and (iii) generate a map based at least in part on the updated estimated missing information, the at least one of the second plurality of k-space images corresponding thereto, and the baseline k-space image corresponding to the at least one of the second plurality of k-space images. The computation unit may be further configured to computationally estimate the missing information based at least in part on a default value, a portion of one of the corresponding baseline k-space images or a different one of the second plurality of k-space images.

In some embodiments, the map comprises at least one of an anatomical image or a thermal map of the target region. Each of the baseline k-space images may comprise a plurality of pixels, and the computation unit may be further configured to update the estimated missing information based at least in part on the magnitude associated with a pixel in one of the baseline k-space images.

The system may include first and second MRI coils, where each of the baseline k-space images and each of the second plurality of k-space images is associated with the first and/or second MRI coil. In some embodiments, the computation unit is further configured to (a) computationally reconstruct a plurality of baseline images from the plurality of baseline k-space images, and (b) for each one of the second plurality of k-space images, computationally reconstruct an image in a third image set based at least in part on the computationally estimated missing information associated therewith.

In various embodiments, each of the baseline k-space images is acquired from an echo in response to the first multi-echo pulse sequence and each of the second plurality of k-space images is acquired from an echo in response to the second multi-echo pulse sequence. The computation unit may be further configured to correspond each reconstructed image in the third image set to one of the reconstructed baseline images based at least in part on echo times of the echoes associated therewith.

The system may further comprising a plurality of MRI coils, where each of the baseline k-space images and each of the second plurality of k-space images are associated with at least one of the MRI coils. The computation unit may be further configured to relate each reconstructed image in the third image set to one of the reconstructed baseline images based at least in part on the associated at least one MRI coil. The echo time associated with the reconstructed image in the third image set may be the same as the echo time associated with the corresponding reconstructed baseline image.

In some embodiments, the computation unit is further configured to determine a phase difference between a pixel in one of the reconstructed baseline images and the corresponding pixel in the corresponding reconstructed image in the third image set. The computation unit may be further configured to update the phase difference based at least in part on the echo time of the k-space image from which the corresponding reconstructed image in the third image set is reconstructed. The phase differences associated with the reconstructed images in the third image set may positively correlate with the echo times of the second plurality of k-space images.

In various embodiments, the computation unit is further configured to update the phase difference based at least in part on the echo times associated with at least two different images in the second plurality of k-space images. Alternatively or in addition, the computation unit may be further configured to update the corresponding reconstructed image in the third image set based at least in part on the updated phase difference, and transform the updated image to a k-space image in a fourth image set. Still further, the computation unit may be configured to update the k-space image in the fourth image set based at least in part on the corresponding image in the second plurality of k-space images acquired at a same echo time.

In some embodiments, the computation unit is configured to iteratively perform various steps until a termination condition is satisfied. The termination condition may be one or more of a number of iterations exceeding a predetermined limit, or a change in the updated k-space image in the fourth image set or in the reconstructed image in the third image set between two iterations is below a predetermined minimum. The computation unit may be configured to execute a machine learning algorithm, such as an artificial neural network (e.g., a convolutional or recurrent neural network) for performing various steps.

In some embodiments, the computation unit is configured to computationally reconstruct an image in a fifth image set based at least in part on the updated k-space image in the fourth image set and computationally reduce noise from the reconstructed image in the fifth image set. The computation unit may be configured to apply a locally low-rank regularization to at least two of the images in at least one of the third image set or the fifth image set for reducing the noise therein.

Methods implementing the operations described above are also within the scope of the present invention.

As used herein, the terms "approximately," "roughly," and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
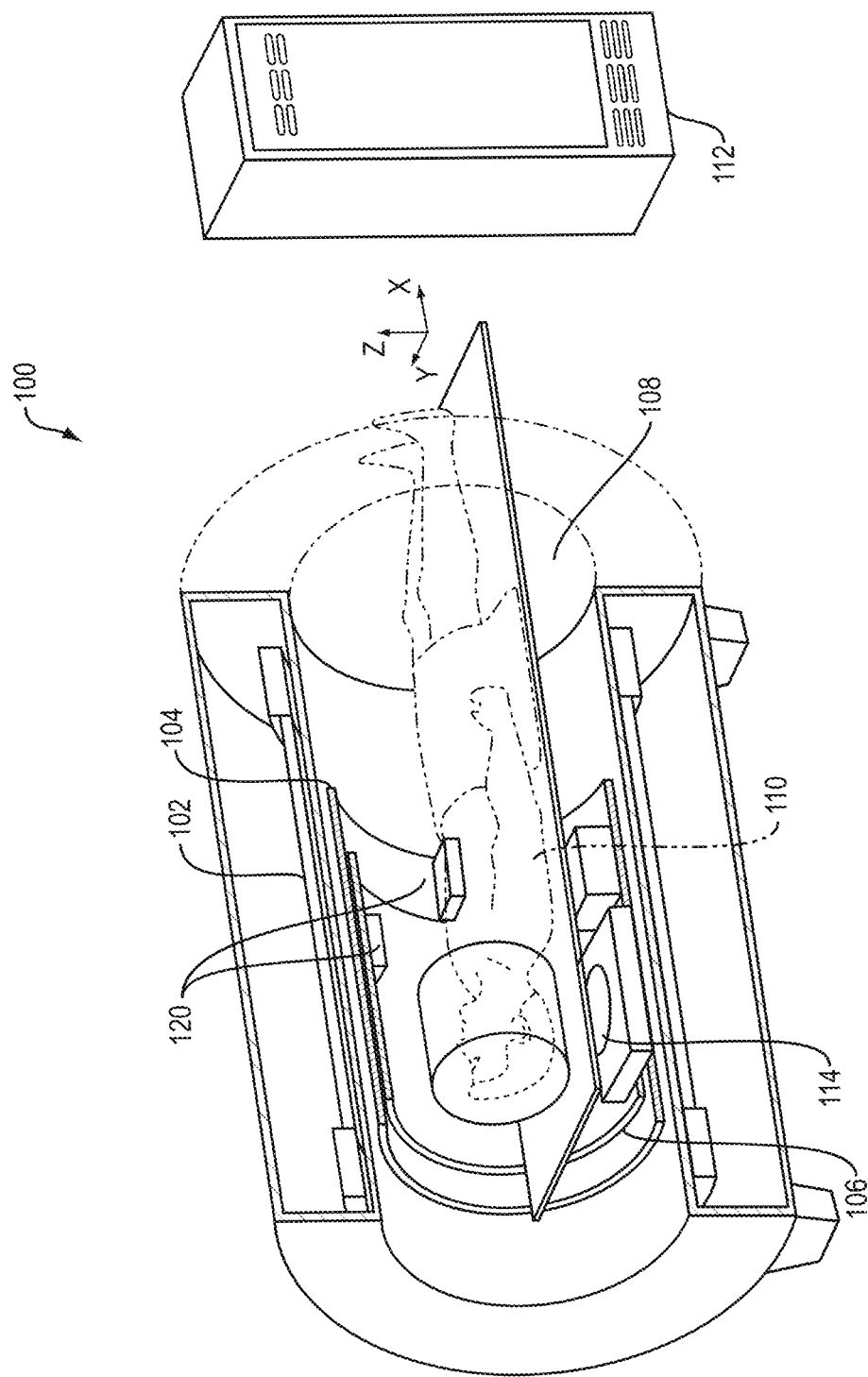
FIG. 1 cross-sectionally depicts a representative MRI apparatus.

The present invention provides systems and methods for monitoring a target (e.g., a treatment target) or other objects of interest in a region of interest in real time during an image-guided treatment/diagnosis procedure. The procedure may, for example, involve the application of focused ultrasound to (i.e., the sonication of) a material, a tissue or organ for the purpose of heating it, either to necrose, ablate, or otherwise destroy the tissue if it is, e.g., cancerous, or for non-destructive treatments such as pain amelioration or the controlled inducement of hyperthermia. Ultrasound may also be used for other, non-thermal types of treatment, such as, e.g., neuromodulation. Alternatively, the procedure may use different forms of therapeutic energy, such as, e.g., radio-frequency (RF) radiation, X-rays or gamma rays, or charged particles, or involve other treatment modalities such as cryoablation. Monitoring the temperature and/or location of the target in various treatment procedures may serve to guide the therapeutic energy beam to the target and/or around other, non-target tissues and organs, i.e., to adjust the beam focus, profile, and/or direction based on images of the affected anatomical region, which may, in some embodiments, also visualize the beam focus. MRI is a widely used technique for such image-based thermal and/or motion tracking. However, other imaging techniques, including, e.g., X-ray imaging, X-ray computed tomography (CT), or ultrasound imaging, may also be used and are within the scope of the present invention. In addition, the temperature and/or motion monitoring may be achieved using one or more two-dimensional images and/or three-dimensional images. MRI systems in which the techniques described herein may be implemented are well-known in the art; an exemplary system is shown in FIG. 1.

In some embodiments, imaging during a procedure is simultaneously used to quantitatively monitor in vivo temperatures. This is particularly useful in MR-guided thermal therapy (e.g., MRgFUS treatment), where the temperature of a target treatment area (e.g., a tumor to be destroyed by heat) should be continuously monitored in order to assess the progress of treatment and correct for local differences in heat conduction and energy absorption to avoid damage to tissues surrounding the treatment area. The monitoring (e.g., measurement and/or mapping) of temperature with MR imaging is generally referred to as MR thermometry or MR thermal imaging.

Figure 2A:
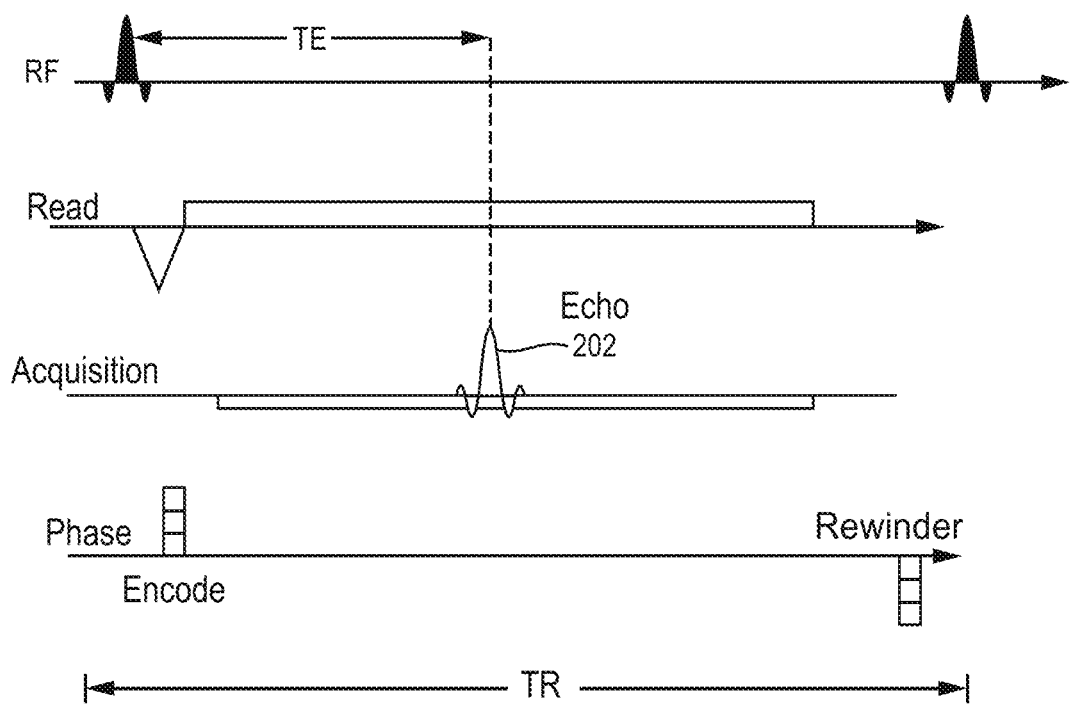
FIG. 2A depicts an exemplary single-echo GRE pulse sequence for PRF thermometry.

Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change—i.e., a treatment image—thereby capturing a small phase change that is proportional to the change in temperature. A map of temperature changes may then be computed from the (reconstructed) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo). FIG. 2A depicts an exemplary single-echo GRE pulse sequence for PRF thermometry, where only one echo 202 is acquired (at TE) between the successive pulse sequences (i.e., the repetition time or TR).

Figure 2B:
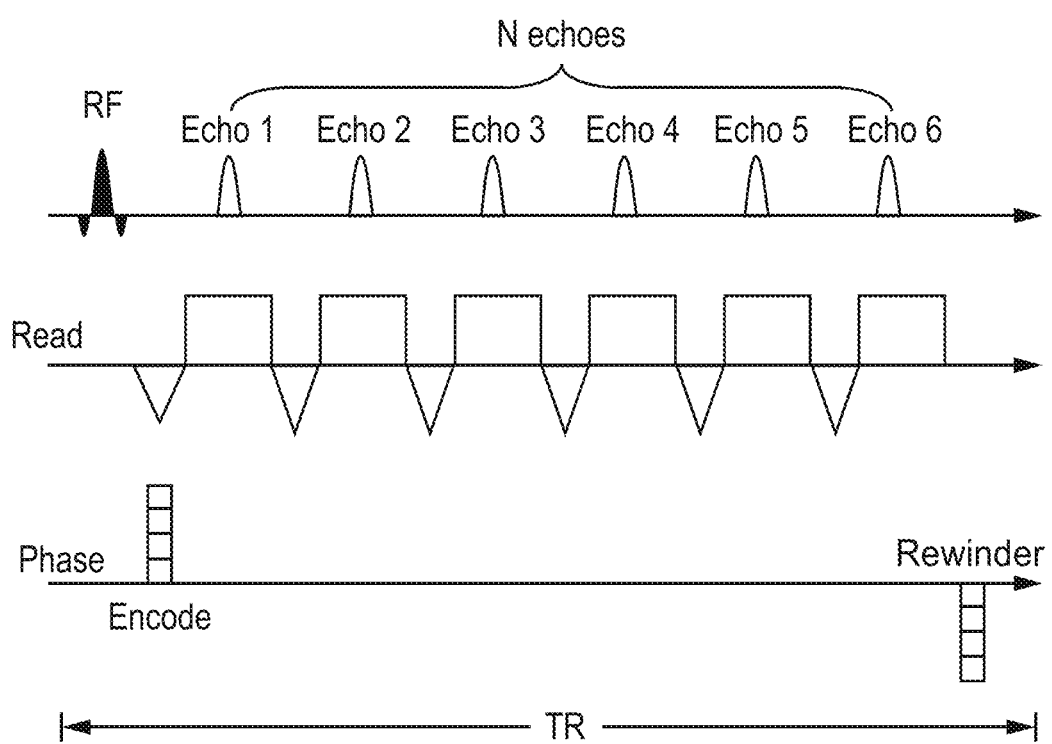
FIG. 2B depicts a multi-echo GRE pulse sequence in which echoes in an echo train are acquired.
Figure 2C:
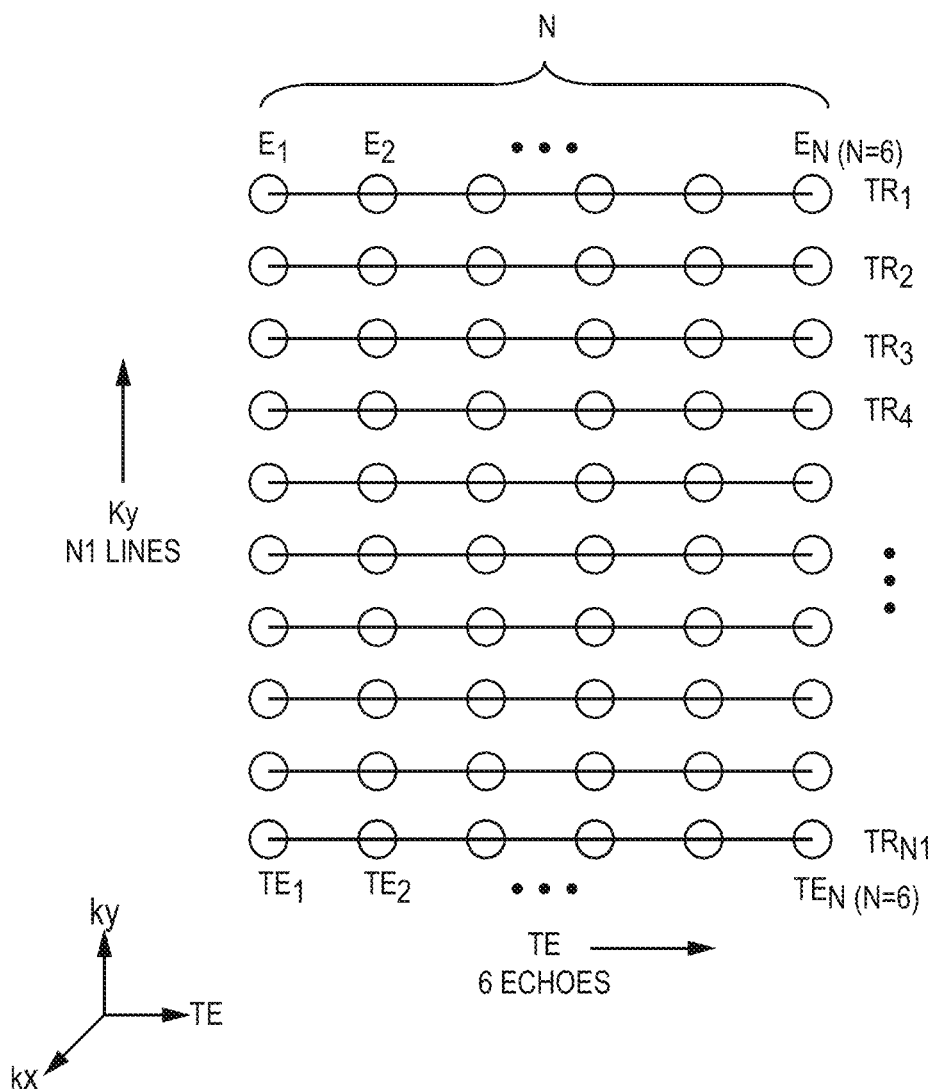
FIG. 2C depicts a fully sampled data set of an image slice acquired using a multi-echo GRE pulse sequence.

In typical MR images acquired using the single-echo GRE pulse sequence, a spatial shift Ar caused by field inhomogeneity may exist. Increasing the bandwidth of the MR receiver tends to reduce the spatial shift, but at the price of increasing the standard deviation (or the measurement error) of the temperature. As a result, choice of the bandwidth reflects a trade-off between minimizing the spatial shift and reducing the measurement error. To address this challenge, in some embodiments, the MRI system uses receivers with high bandwidth and applies a multi-echo GRE pulse sequence for PRF thermometry. For example, referring to FIG. 2B, in a multi-echo GRE pulse sequence, N echoes (N=6 as depicted) in an echo train may be acquired within each TR. Because each echo is acquired within a relatively short time window with a high receiver bandwidth, the spatial shift Ar may be negligible. In addition, by combining (or averaging) the received signals from all N echoes, the signal-to-noise ratio (SNR) of the received MR signals may be improved, which in turn reduces the measurement error of the temperature. FIG. 2C depicts a fully (or "completely") sampled data set of an imaging slice acquired using the multi-echo GRE pulse sequence. As depicted, each row is associated with a phase-encoding step, $k_y$, acquired in one TR (and $k_x$, which is perpendicular to the plane and thus not shown, is associated with a number of MR signal readouts); in addition, multiple echoes, N, are acquired in each TR, and each echo, $E_i (i \leq N)$, is acquired at a time of $TE_i$. Assuming that each imaging slice includes $N_1$ phase-encoding steps and N2 readouts, the fully sampled dataset of a slice includes $N_1 \times N_2 \times N$ data points. In conventional MR thermal scanning for a neuro system, TR=27 milliseconds and $N_1$=128; thus, it may take up to 3.5 seconds to acquire a single slice of the MR image. While this scan rate may be acceptable for acquiring the baseline PRF phase images prior to commencing the ultrasound procedure, it may be too slow to assess the progress of treatment and avoid damage to tissues surrounding the target region in real time during the ultrasound procedure when the temperature at the ultrasound focus (which generally coincides with the target treatment region) increases rapidly. The term "fully sampled data set" herein refers not only to a data set that is fully sampled but also to an undersampled data set for which the full data set can be generated or estimated.

Figure 3:
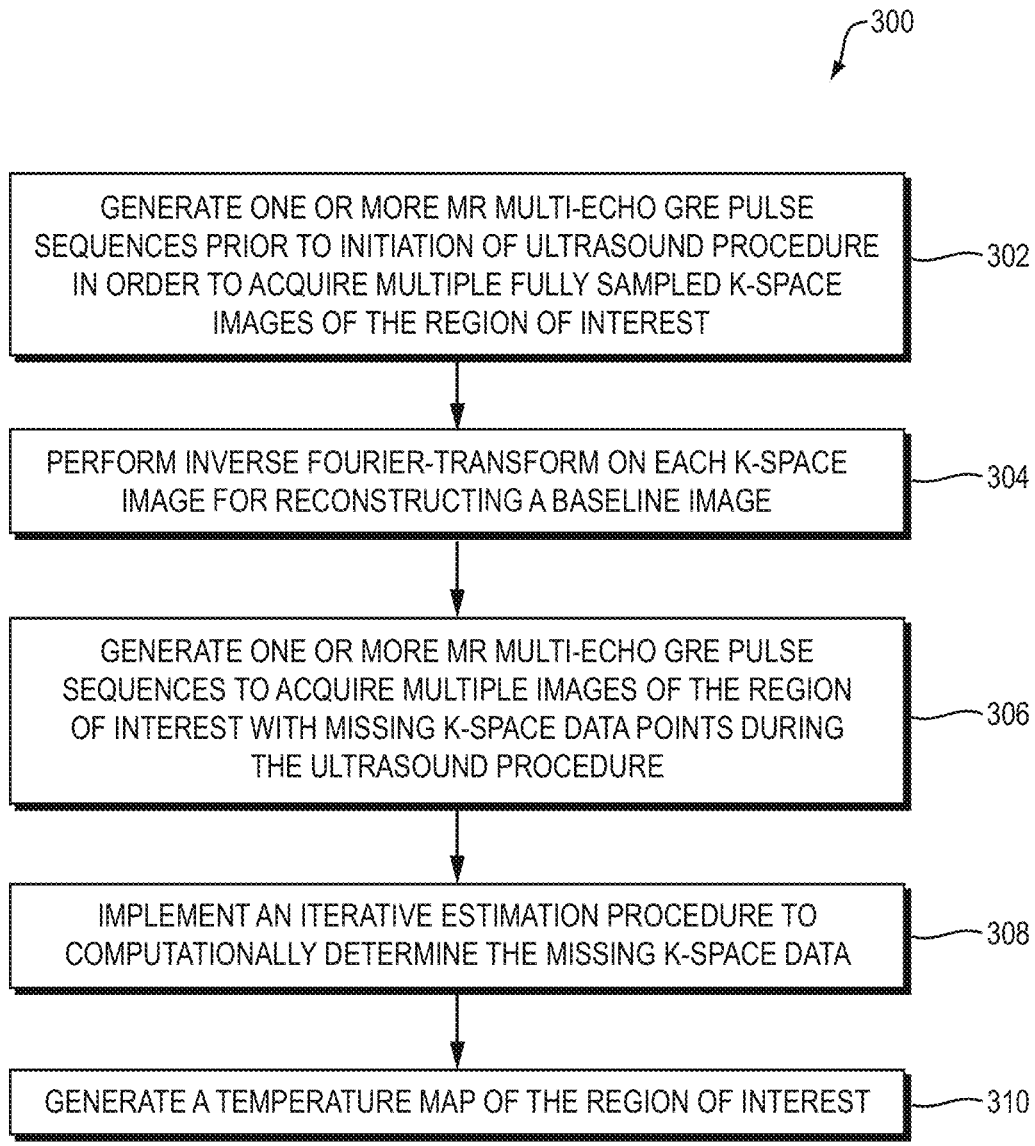
FIG. 3 is a flowchart illustrating an exemplary approach to accelerated MR thermometry in accordance with various embodiments.

Accordingly, the fully sampled k-space data set depicted in FIG. 2C may be acquired only prior to the ultrasound procedure; during the ultrasound procedure, only partial raw k-space data is acquired to provide real-time (or at least accelerated) MR thermometry as further described below. FIG. 3 illustrates an exemplary approach 300 to accelerated MR thermometry in accordance with various embodiments. The method includes preparatory steps performed prior to the ultrasound procedure of interest, as well as steps executed during the procedure. In a first preparatory step 302, one or more MR multi-echo GRE pulse sequences are generated prior to initiation of ultrasound treatment or diagnosis in order to acquired multiple fully sampled k-space images of the region of interest (e.g., the treatment region); each image corresponds to an echo $E_i$ received at an echo time $TE_i$, and different images may be acquired using the same or different MR coils 104. In a second preparatory step 304, each k-space image is inverse Fourier-transformed to reconstruct an image, which can then be utilized as a baseline reference image. After initiation of treatment/diagnosis, one or more MR multi-echo GRE pulse sequences may be generated to acquire multiple images of the region of interest (in step 306); again, each treatment image corresponds to an echo $E_i$ acquired at time $TE_i$. In one implementation, each treatment image has an echo time $TE_i$ corresponding to that of the baseline reference image. In addition, only partial raw k-space data is acquired in at least one of the echoes of the treatment image in order to reduce the data acquisition time, thereby allowing real-time monitoring of the tissue state (e.g., temperature) in the region of interest (e.g., the treatment region). (Partial raw k-space data may be acquired by "under-sampling" to obtain less than the entire k-space image data as is done in step 302.) For example, in the fully sampled k space data shown in FIG. 2C, each echo in each TR is sampled at all $N_1$ values of $k_y$.

When undersampling the data, all the echoes are sampled during each TR, but different phase-encoding values are missing. For example, in FIG. 4A, all 6 echoes are sampled in each TR, but only odd $k_y$ values are sampled by echoes 402, and only even $k_y$ values by echoes 408. Since the $k_y$-echo matrix in FIG. 4A is half empty, the number of TRs (and therefore the scan time) is reduced by a factor R=2 compared to the fully sampled $k_y$-echo matrix depicted in FIG. 2C.

Figure 4A:
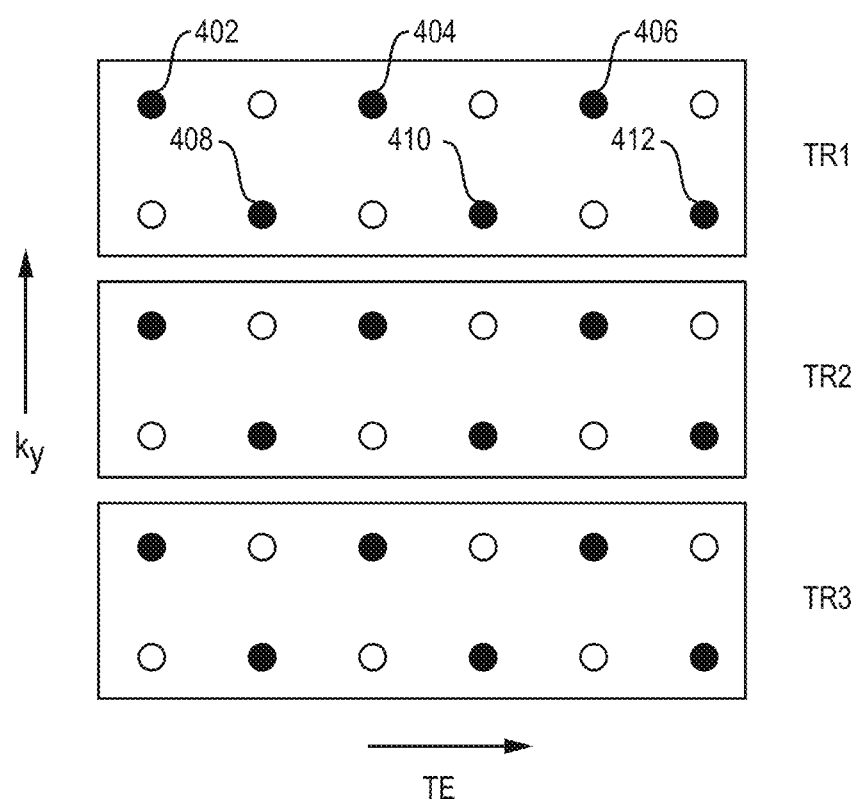
FIG. 4A depicts a data set of an image slice acquired using a multi-echo GRE pulse sequence with some data missing.
Figure 4B:
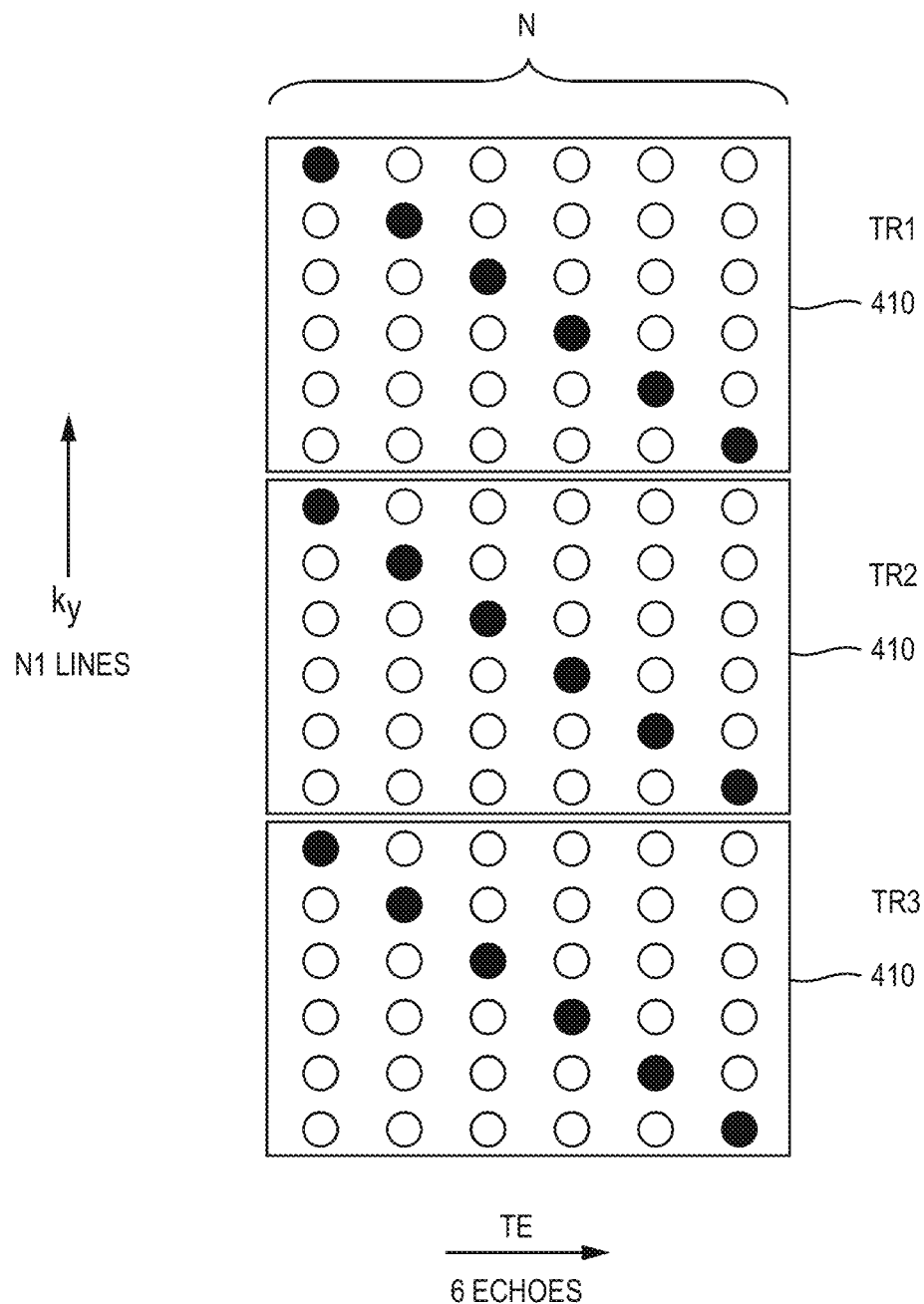
FIG. 4B depicts an exemplary approach for under-sampling the k-space data in accordance with various embodiments.
Figure 4C:
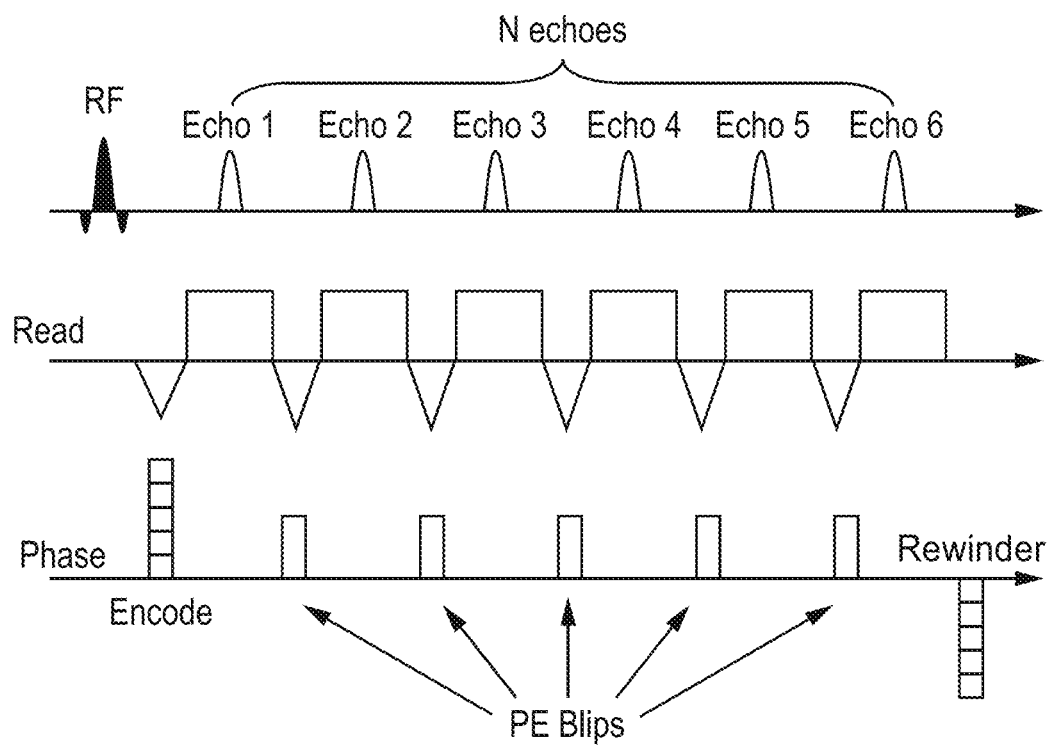
FIG. 4C depicts a set of $G_y$ gradient blips implemented to acquire echoes having multiple phase-encoding values in one TR as shown in FIG. 4B.

FIG. 4B depicts another exemplary approach for undersampling the k-space data in accordance with various embodiments. As depicted, the N echoes in each TR 410 are acquired in an interleaved manner such that they all have different phase-encoding values and correspond to different TE times. This approach thus further reduces the data acquisition time by a factor of six (e.g., only three TRs are required to acquire data having eighteen phase-encoding values). Referring to FIG. 4C, in various embodiments, a set of $G_y$ gradient blips is implemented to acquire the echoes having multiple phase-encoding values in one TR (as depicted in FIG. 4B). As shown, each gradient blip may be introduced between the acquisition times of two echoes.

Thus, MR scanning utilizing the approaches described above may require acquisition of only $N_1/R$ (where R represents the imaging acceleration factor and is equal to 2 and 6 in FIGS. 4A and 4B, respectively) phase-encoding lines for each dataset of an imaging slice; this allows R slices to be acquired in 3 seconds and effectively increases repetition time to TR×R milliseconds. In conventional MR thermal scanning for a neuro system where TR=27 milliseconds and $N_1$=128, under-sampling the k-space data as depicted in FIG. 4B advantageously allows six slices of the MR images to be acquired within 3 seconds (each slice having 21 phase-encoding lines) with TR of 162 milliseconds; by contrast, only one slice can be acquired within 3 seconds in conventional approaches. In addition, increasing TR using the under-sampling approaches described above may significantly improve the quality of MR signals from the body tissue (e.g., brain) due to less $T_1$ signal saturation. For example, the SNR of the brain MR signals may be increased by a factor of 1.9 by increasing TR from 27 milliseconds (in conventional MR scanning) to 162 milliseconds (in FIG. 4B).

Figure 4D:
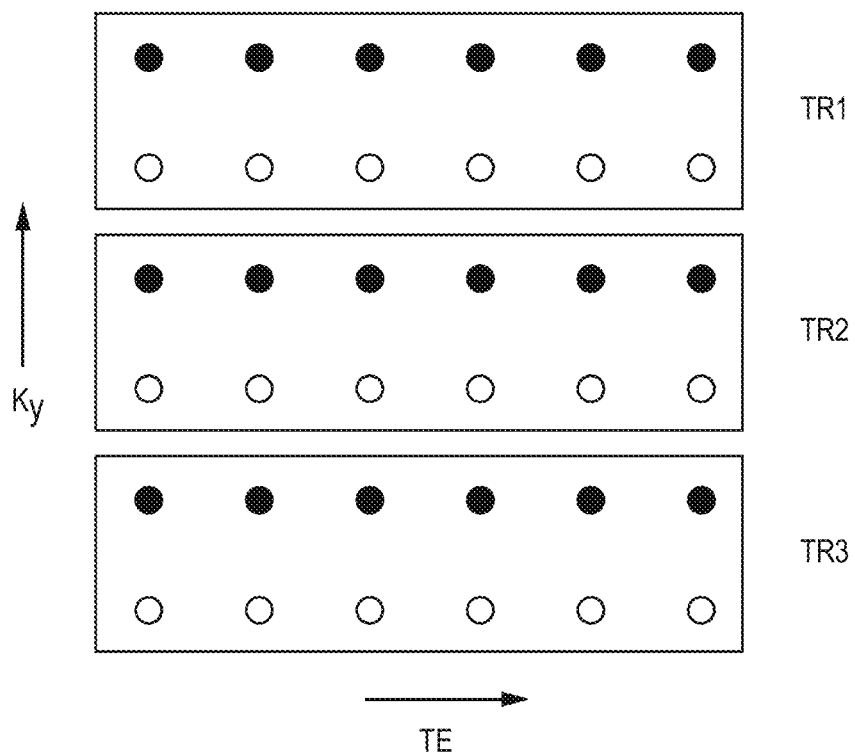
FIG. 4D illustrates another k-space data trajectory useful in some embodiments.

It should be noted that the k-space data trajectories including multiple echoes in each TR 410 as illustrated in FIGS. 4A and 4B represent exemplary embodiments only; other trajectories established by selecting the phase-encoding values and TE times of the received echoes may be suitable for acquiring MR data with an accelerating rate and therefore are within the scope of the present invention. For example, the trajectory depicted in FIG. 4D may be used in some embodiments. Alternatively, the N echoes acquired in each TR 410 may be selected randomly. In addition, the data trajectory in each TR 410 may be the same or different from that in another TR 410.

Figure 5A:
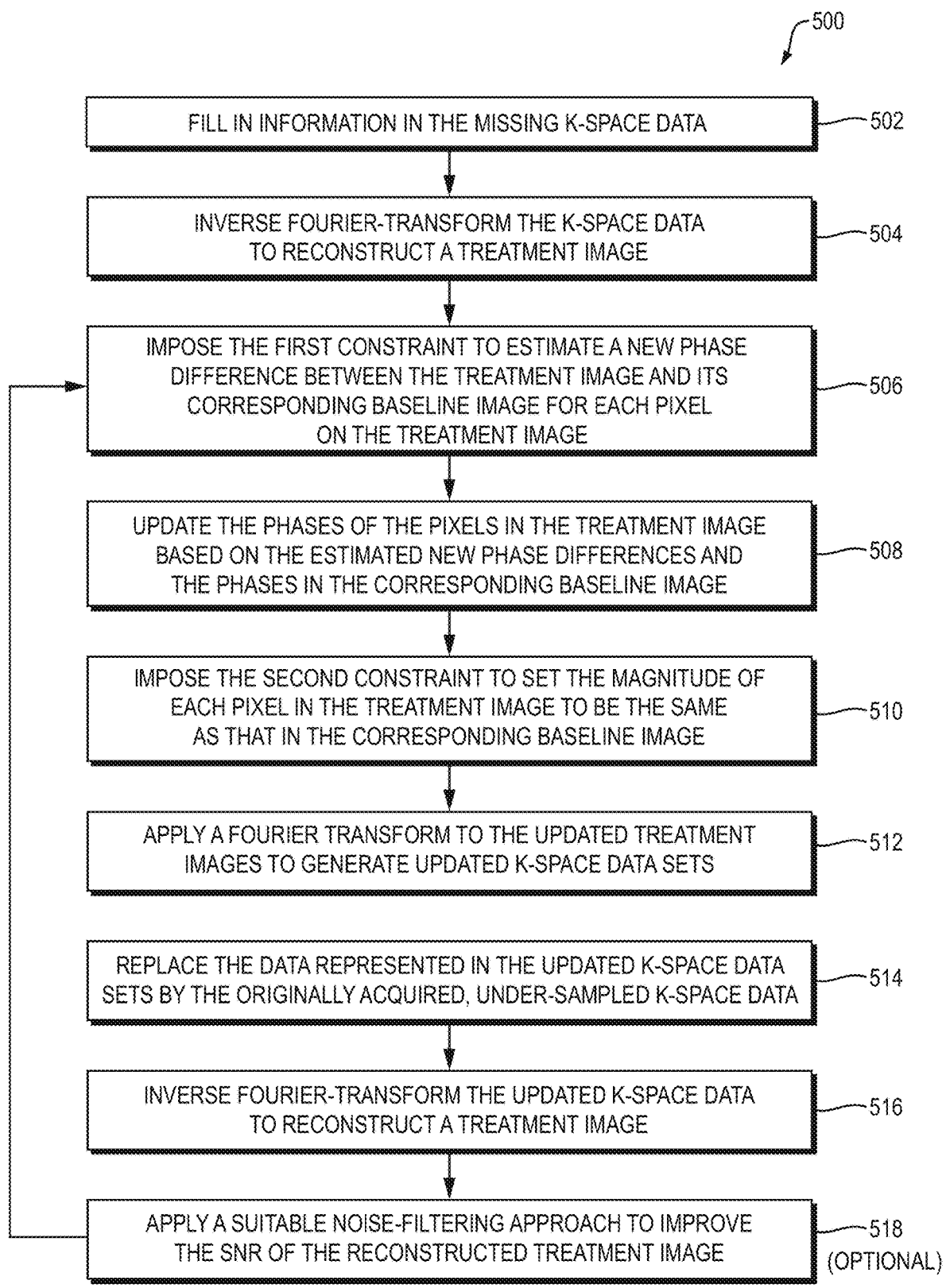
FIG. 5A is a flowchart representing an exemplary approach for performing an iterative estimation procedure in accordance with various embodiments.

Referring again to FIG. 3, in various embodiments, an iterative estimation procedure is implemented to computationally determine the missing k-space data based on one or more constraints as further described below (step 308). FIG. 5A depicts an exemplary approach 500 for performing the iterative estimation procedure in accordance herewith. For example, in a first step 502, the missing k-space data may be initially estimated based on the data acquired from one or more echoes (e.g., an average thereof) in the same echo train. Additionally or alternatively, the missing k-space data may be estimated initially based on the k-space data acquired from the echo(es) at the same echo time, $TE_i$, but in a different echo train or different treatment image and/or in a baseline image. In some embodiments, the missing k-space data can be initially filled in with one or more zeros or any arbitrary numbers. The acquired (or sampled) k-space data and the estimated data then form a full (or complete) set of k-space data, $K_{treatment}(k_y, k_x, echo)$, which can be inverse Fourier-transformed to reconstruct an treatment image, $X_{treatment}(y, x, echo)$ (in step 504):

$$K_{treatment}(k_y,k_x,\text{echo}) \overset{FFT}{\Longleftrightarrow} X_{treatment}(y,x,\text{echo}) \qquad \text{Eq. (1)}$$

In some embodiments, the iterative estimation procedure then imposes one or more constraints on the datasets so as to accurately estimate the missing k-space data. In one embodiment, the constrains are based on prior knowledge about the treatment images. The signal of an echo $E_i$, $S_{i,baseline}$, at a pixel (x, y) on the baseline image that has a magnitude $\rho_i$ (x, y) and a phase $\phi_i$ (x, y) can be represented as:

$$S_{i,baseline}=\rho_i(x,y)\cdot\exp[i\phi_i(x,y)] \qquad \text{Eq. (2)}$$

When the temperature increases ΔT in the region of interest during treatment, the signal of an echo $E_i$, $S_{i,treatment}$, at the pixel (x, y) of the treatment image can be represented as:

$$S_{i,treatment}=S_{i,baseline}\cdot\exp(i\Delta\phi_i)=S_{i,baseline}\cdot\exp(i2\pi K\Delta T\cdot TE_i) \qquad \text{Eq. (3)}$$

where K=0.01 ppm/° C. Thus, the phase difference of the echo $E_i$ (i.e., $\Delta\phi_i$) between the treatment image and the corresponding baseline image may positively (e.g., linearly) correlate to the echo time $TE_i$ of the echo:

$$\Delta\phi_i = \angle(S_{i,treatment}\cdot S^*_{i,baseline})=2\pi K\Delta T E_i \qquad \text{Eq. (4)}$$

Accordingly, the first constraint imposed by the iterative estimation procedure 500 may be the linear relationship between the echo time TE and the phase difference between the treatment image and corresponding baseline image. Referring again to FIG. 5A, in one embodiment, the iterative estimation procedure first computes the phase differences, Δφ(x, y, echo), between the treatment image and its corresponding baseline image on a pixel-by-pixel basis, and subsequently estimates a new phase difference, $\Delta\phi_{new}$, for each pixel (x, y) of the treatment image such that the new phase differences of the pixels in the treatment image are linear to the echo times TE and are as close as possible to the computed phase differences, Δφ(x, y, echo) (in step 506):

$$\Delta\phi_{new}=F_0(y,x)+(y,x)\cdot TE\approx\Delta\phi(y,x,\text{echo}) \qquad \text{Eq. (5)}$$

where $F_0$ and $F_1$ are two coefficients independent of TE. For example, the signal of an echo Ej associated with the baseline image may be represented as:

$$\rho_{j,baseline}\cdot\exp[i\phi_{j,baseline}] \qquad \text{Eq. (6)}$$

The signal of the echo Ej associated with the treatment image may be represented as:

$$\rho_{j,treatment}\cdot\exp[i\phi_{j,treatment}]. \qquad \text{Eq. (7)}$$

Thus, for each location (x, y), a vector $d_j$ may be defined for echoes $E_j$ (j=1 to N):

$$d_j \equiv \rho_{j,treatment}\cdot\exp[i\phi_{j,treatment}]\cdot\exp-i\phi_{j,baseline}] = \rho_{j,treatment}\cdot\exp[i(\phi_{j,treatment}-\phi_{j,baseline})] \qquad \text{Eq. (8)}$$

Based on Eq. (4), $(\phi_{j,treatment}-\phi_{j,baseline})$ can be represented as:

$$\phi_{j,treatment}-\phi_{j,baseline}=\Delta\phi_j=2\pi K\Delta T\cdot TE_j=F_0+F_1\cdot TE_j \quad \text{Eq. (9)}$$

Subsequently, we can define a vector $v_k$ with N−1 components based on the vector $d_j$ in Eq. (8):

$$v_k=d_{j+1}\cdot d^*_j=\rho_{j,treatment}^2\cdot\exp(iF_1\cdot\Delta TE), \text{ where } j \text{ and } k=1 \text{ to } N-1 \quad \text{Eq. (10)}$$

where $\Delta TE$ represents a TE increment between two neighboring echoes. Because the phase in Eq. (10) is independent of k, $F_1$ can be represented as:

$$F_1=\frac{\sphericalangle[\text{mean}(v)]}{\Delta TE} \quad \text{Eq. (11)}$$

where $\sphericalangle$ represents the four-quadrant arctangent operator and mean represents the mean over all the components of v.

In addition, we can define another vector u with N components based on the vector d and the known $F_1$. The jth component of u, $u_j$, is given by:

$$u_j=d_j\cdot\exp(-iF_1\cdot TE_j)=\rho_{j,treatment}\cdot\exp(iF_0), j=1 \text{ to } N$$

Because the phase of $u_j$ is independent of j, $F_0$ can be represented as:

$$F_0=\sphericalangle[\text{mean}(u)] \quad \text{Eq. (12)}$$

Based on Eqs. (11) and (12), the two coefficients, $F_0$ and $F_1$, can be computed. As further described below, accurate values of $F_0$ and $F_1$ may be obtained after reasonable convergence of the estimated data is achieved. In various embodiments, the new phase differences estimated based on $F_0$ and $F_1$ together with the phases in the corresponding baseline image may then be utilized to update the phases of the pixels in the treatment image on a pixel-by-pixel basis (in step 508). For example, the signal of an echo Ej in the treatment image may be updated as:

$$\rho_{j,treatment}\cdot\exp[i\phi_{j,baseline}]\cdot\exp[i(F_0+F_1\cdot TE_j)] \quad \text{Eq. (13)}$$

In addition, because the temperature increase resulting from the ultrasound procedure affects mostly the phases of the pixels in the treatment images, the iterative estimation procedure may impose the second constraint, which sets the magnitude of each pixel in the treatment image to be the same as that in the corresponding baseline image (in step 510):

$$|X_{treatment}(y,x,\text{echo})|\rightarrow|X_{baseline}(y,x,\text{echo}) \quad \text{Eq. (14a)}$$

Additionally or alternatively, the fact that the spin density $\rho_{treatment}$ decreases during heating by 10%-15% relative to $\rho_{baseline}$ (due to lengthening of T1 by about 25% resulting from heating to 20° C. above body temperature) can be taken into account. Hence the signal of echo j during treatment in Eq. (13) can be written as $$S_{j,treatment}=\rho_{j,baseline}\cdot A\cdot\exp(i\phi_{j,baseline})\cdot\exp[(F_0+F_1\cdot TE_j)] \quad \text{Eq. (14b)}$$

where A (which is smaller than 1) is a real positive number that represents this decrease in signal amplitude. A depends on x, y but is independent of echo time. From Eqs (6) and (14) and the fact that A is the same for all TE we conclude that $$A(y,x)=\text{mean}\left(\frac{\|S_{j,treatment}\|}{\|S_{j,baseline}\|}\right) \quad \text{Eq. (14c)}$$

where $S_{j,treatment}$ and $S_{j,baseline}$ are the treatment and baseline signals at echo j and ⟦ # ⟧ represent the magnitude of the signal inside the brackets. The mean in Eq. (14a) is the mean over all the echoes and coils, since A is the same for all echoes and coils. During each iteration we calculate A using Eq. (14a) and then substitute it in Eq. (14b). Since A is spatially slowly varying, a standard Total Variation (TV) operator may be used to smooth it and improve its accuracy. The calculated signal $S_{j,treatment}$ in Eq. (14b) is imposed in step 510 in FIG. 5A. During the iterations, $F_0$, $F_1$ and A converge to the correct value. Alternatively or additionally, the effect of the chemical shift caused by heating that changes the resonance frequency can be integrated in the Eq. (14b) in addition to or instead of the amplitude change. Additionally or alternatively, the model can be extended to account for fat by using the well-known technique of "water fat separation" on both baseline and treatment images.

Figure 5B:
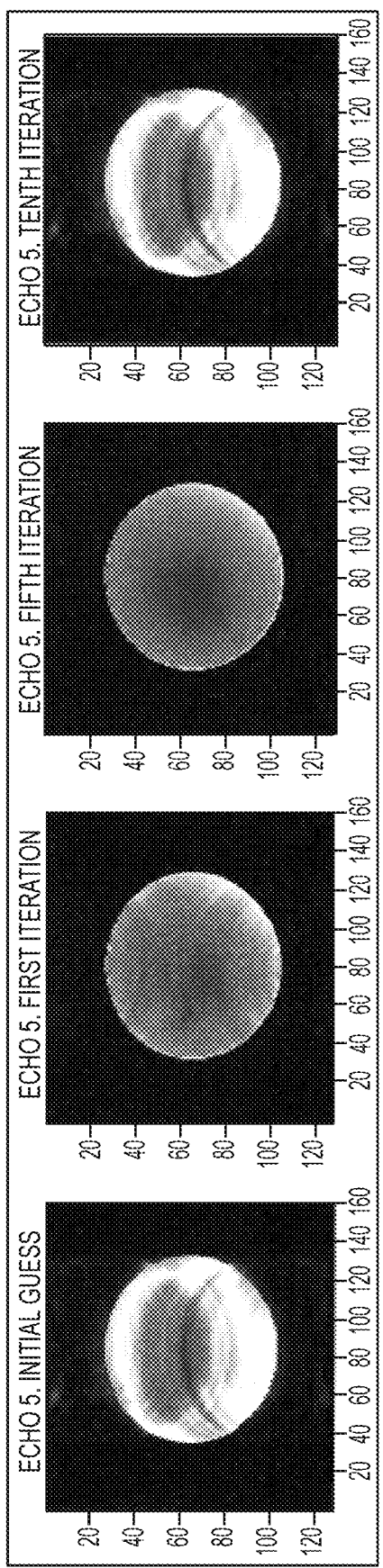
FIG. 5B depicts the improvement in image quality from iteration to iteration using the estimation approach set forth in FIG. 5A.

After the above constraints are imposed, the iterative estimation procedure may apply a Fourier transform to the updated treatment images to generate updated k-space data sets (in step 512). In some embodiments, the iterative estimation procedure imposes a third constraint that replaces the updated k-space data sets by the originally acquired, under-sampled k-space data (in step 514):

$$K(k_y s,k_x s,\text{echo})\rightarrow K_{samp}(k_y s,k_x s,\text{echo}) \quad \text{Eq. (15)}$$

where $K_{samp}$ represents the originally acquired k-space data at various locations, $k_y s$ and $k_x s$. Thus, after step 514, the k-space data sets include the data acquired from the echoes as well as the data estimated based at least in part on the echo times as described above. After step 514, the k-space data can be inverse Fourier-transformed to reconstruct a treatment image (in step 516). Steps 504-516 may be iteratively performed until a termination condition (e.g., the image difference between two consecutive iterations are below a predetermined threshold or a certain number of iterations have been performed) is satisfied, indicating that the missing k-space data has been properly estimated. Thus, by imposing the constraints in a repetitive, alternative manner as described above, a proper estimation of the missing k-space data can be achieved. In some embodiments, the iterative estimation procedure may use a convolutional or recurrent neural network trained to determine the missing k-space data (see, e.g., https://arxiv.org/pdf/1712.02862.pdf, which is incorporated herein by reference). FIG. 5B depicts improvement in image quality from iteration to iteration using the estimation approach 500.

Referring again to FIG. 5A, after the third constraint is imposed to replace the updated k-space data sets by the originally acquired, under-sampled k-space data, an optional step 518 may be performed to improve the SNR of the reconstructed treatment images using a suitable noise-filtering approach. For example, because each location (y, x) in the image dataset X has N (i.e., the number of echoes) points that are highly correlated spatially (which means that all the echoes correspond to the same anatomy), in various embodiments, the noise-filtering approach implements a locally low-rank (LLR) regularization that exploits spatial correlation to reduce the noise level of the treatment images. Approaches for using LLR regularization for improving the SNR of the images are provided, for example, in journal publications such as "Accelerating Parameter Mapping with a Locally Low Rank Constraint," by T. Zhang et al., Magnetic Resonance in Medicine, volume 73, 655-661 (2015) and "A Singular Value Thresholding Algorithm for Matrix Completion" by J. F. Cai et al, SIAM Journal on Optimization, volume 20(4), 1956-1982 (2010), the entire disclosures of which are incorporated herein by reference. In one embodiment, step 518 is performed only in the last 5-10 iterations. Typically, the SNR of the computed temperature may be improved by a factor of two using LLR regulation. Additionally or alternatively, a wavelet transform can be used for noise-filtering.

It should be noted that the second constraint that sets the magnitude of each pixel in the treatment image to be the same as that in the corresponding baseline image may be relaxed in some embodiments. For example, this constraint may be imposed in the first few iterations (e.g., 1-5 iterations) only; after reasonable convergence of the estimated data is achieved, this constraint may be removed (i.e., step 510 may be skipped after the first few iterations). Thus, the magnitudes of the pixels in the treatment images may be proximate to, but not necessarily identical to, those in the corresponding baseline reference images.

Subsequently, the treatment images may be compared against the corresponding baseline images to computationally generate a temperature map of the region of interest, thereby providing real-time monitoring of the temperature change during the ultrasound procedure (step 310). In one embodiment, the temperature map is generated by weighting the computed temperature change, $\alpha T_i$, associated with each echo $E_i$ in the echo train using a weighting function W. As described above, the temperature change, $\alpha T_i$, may be computed based on the phase difference, $\Delta \phi_i$, between the image acquired from echo $E_i$ (at echo time $TE_i$) and its corresponding baseline image:

$$\Delta T_i = \frac{1}{2\pi \cdot K} \frac{\Delta \Phi_i}{TE_i} \quad i = 1 \text{ to } N$$

A weighted combination of the temperature change, $\Delta T_i$, associated with each echo may then be computed to determine the temperature change associated with the treatment image:

$$\Delta T = \frac{\sum_{i=1}^{N} w_i \cdot \Delta T_i}{\sum_{i=1}^{N} w_i} \quad \text{Eq. (16)}$$

Steps 306-310 may be iteratively performed throughout the ultrasound procedure for monitoring the region of interest during the procedure.

Accordingly, various embodiments of the present invention may efficiently increase the MR imaging rate (e.g., by under-sampling the k-space data in one or more echoes in a multi-echo GRE pulse sequence) while providing images with sufficient resolution (e.g., by properly determining the missing (or non-acquired) k-space data using the constraint(s) and iterative estimation approach described above) for monitoring the region in real time during the ultrasound procedure.

Figure 6:
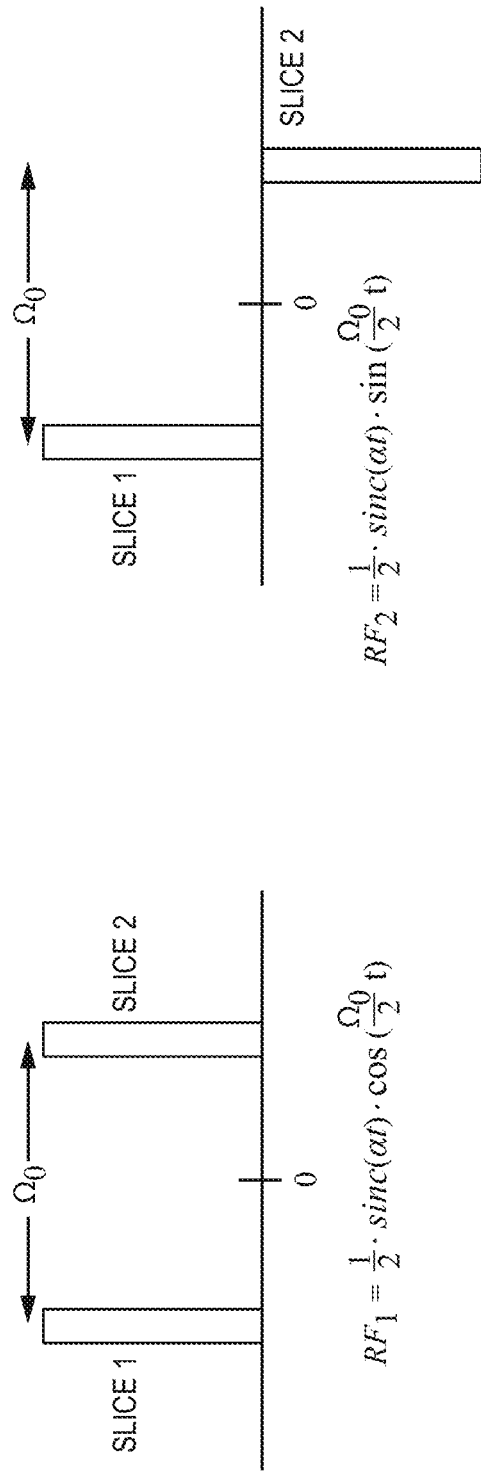
FIG. 6 graphically depicts an exemplary approach for applying two RF-pulses having a frequency difference therebetween to simultaneously acquire two slices having different phases.

In the examples given above, only a single slice is excited in a given TR. Hence, when a total scan time of 3 seconds is desired, with an acceleration of R, the number of TR's is reduced by a factor of R; as a result, the TR increases by R. For example, as shown above, TR increases from 27 to 142 milliseconds when R=6; in addition, SNR increases by ~1.9. An alternative approach in accordance with various embodiments excites all the slices simultaneously during each TR. During RF excitation, each slice is excited by a different phase, and the RF waveform is a linear combination of the waveforms required to excite each slice separately. If R slices are excited simultaneously, they overlap one another. To separate them, R waveforms may be applied to acquire R datasets, where the phase of each slice changes linearly from waveform to waveform in a known way. Finally, the slices may be separated by applying an inverse Fourier transform or Hadamard transform on the R datasets. In this case, a short TR of 27 milliseconds may be used to excite all R waveforms. However, since all the slices are simultaneously excited, the SNR increases by $\sqrt{R}$ compared to a single slice with TR=27 milliseconds. This is very beneficial for a large R. For example, for R=8, the SNR gain is $\sqrt{8}=2.8$. FIG. 6 depicts an exemplary approach for applying two RF-pulses, $RF_1$ and $RF_2$, having a frequency difference $\Omega_0$ therebetween to simultaneously acquire two slices that are phase encoded such that there is a phase difference therebetween (e.g., $\pi$). Upon receiving two MR signals, $Sn_1$ and $Sn_2$, the two slices may be separated by using the following equations:

$$\text{Slice}_1 = (S_{n1} + S_{n2})/2,$$

$$\text{Slice}_2 = (S_{n1} - S_{n2})/2.$$

Employing the approaches described above for accelerating the MR imaging rate may advantageously increase the spatial resolution of the images while acquiring a smaller number of slices for each temperature measurement compared to conventional MR scanning approaches. For example, when R=6, it may be possible to acquire three MR imaging slices, each having 256 phase-encoding steps (i.e., $N_1=256$). The images having more phase-encoding steps may then provide a higher spatial resolution compared to the conventional MR images where 128 phase-encoding steps are used. In addition, when desired, the above-described approaches may increase the time resolution of the acquired images (i.e., reduce the time required for each temperature measurement). For example, when R=6, it may be possible to acquire an imaging dataset that has 3 slices in 1.6 seconds. This acquisition rate is faster compared to the conventional approaches where 3 seconds are required to acquire an imaging dataset having one slice.

The approach set forth in Eqs. (14a-14c) can be extended. In one embodiment, where the baseline image is not stable due to field map variations or movement of the water, several baseline images are collected the treatment phase is fitted with a linear combinations of the baseline images. In some embodiments, the approach can be formulated as a const function to be minimized:

$$g = \|\sum_{n}^{Ncoils} \sum_{j}^{Nechoes} (\bar{k}_{n,j} - E_j\{Tx_{n,j}\})\|_2^2 + \lambda \cdot \text{Reg}(x) \quad \text{Eq. (17)}$$

here $\bar{k}_{n,m}$ is the undersampled data for coil n and echo j, $E_j$ is the undersampled encode pattern, for echo j, T is the transformation operator from real space to k space, x is a pixel in real space which is modeled with respect to the baseline pixel to the treatment image, and Reg(x) is a regularization term based on any prior knowledge (Tikhonov, total variation, sparsity, etc.)

One example of such model is where the baseline image is not stable (e.g., due to water movement) and some relaxation of T2* occurs upon heating (R2*=1/T2*). In this case, x can be computed as $$x_{n,j} = (\sum_{l}^{Nb} w_{l,j} \rho_{l,j}) \cdot A \cdot \exp(i\phi_{j,baseline}) \cdot \exp[i(F_0 + F_1 \cdot TE_j)] \cdot \exp[-R^*_2 \cdot TE_j] \quad \text{Eq. (18)}$$

ρ is 1 baseline magnitude at the echoes j and $N_b$ is the number of baselines. Regularization terms can be applied to $F_1$ and/or $F_0$ and/or $R_2^*$ and/or the amplitude A, across the measured spatial locations (either 2D or 3D). Other regulation terms such as LLR can be implemented along the echo train. Additionally or alternatively, the LLR can be applied to the difference between the treatment data and the baseline. Additionally or alternatively, spatio-temporal correlations can be considered using temporally constrained reconstruction (TCR).

Another approach to accommodating missing k-space data is to use a trained neural network, such as a convolutional neural network (CNN) or other neural network architecture that may include fully connected layers; a recurrent neural network (RNN), a "neural in neural" (NiN) network, and others. As is well known, neural networks process information in a manner similar to the human brain. A neural network is composed of a large number of highly interconnected processing elements (neurons) working in parallel to solve a specific problem. Neural networks learn by example; they cannot be programmed to perform a specific task. The examples must be selected carefully, otherwise useful time is wasted or, worse, the network might function incorrectly. Neural networks that operate on the principle of "supervised learning" are trained using labeled input images (with the label specifying a characteristic relevant to the output, e.g., a classification).

In some embodiments, the neural network learns a mapping from aliased images in k-space to artifact-free images in k-space. In one image-driven method for network training, the loss function L includes a regularization term, e.g., $L_{imag} = \|x-y\|_n^n + \lambda Re(x, \theta)$. In this case, n is either 1 or 2 and the regularization parameter, $Re(x, \theta)$, can be derived from relevant prior knowledge about the probability distribution function. In one embodiment, Tikhonov regularization is used for data smoothness.

In other supervised learning approaches, knowledge of the encoding operator $E_j\{\overline{T}(x_{n,j}, \overline{\theta})\}$ is used to find $\overline{x}$ in real space from the given data in k space. In some embodiments, data consistency of the undersampled k-data is taken into account as an additional term for the loss function:

$$L_{us} = \left\| \sum_n^{N_{coils}} \sum_j^{N_{echoes}} (k_{n,j} - E_j\{\overline{T}(x_{n,j}, \theta)\}) \right\|_2^2$$

where $\overline{T}(x_{n,j})$ is the transformation from real space to k space. In DL thermometry, an additional loss function accounting for data consistency of the retrospective baseline (bl) data, $k^{bl}$, may be employed:

$$L_{bl} = \left\| \sum_n^{N_{coils}} \sum_j^{N_{echoes}} (E_j\{k^{bl}_{n,j}\} - E_j\{\overline{T}x^{bl}_{n,j}, \theta\}) \right\|_2^2$$

The encoder operator $E_{j1}$, which represents the k trajectories, can also include free parameters in the neural network architecture (NNA) and can be learned. In some embodiments, the k-space data trajectory of different echoes can be different. In one embodiment, physical constraints are added to the gradient trajectories as loss functions, allowing the k sampling trajectories to be learned. The $E_j$ sampled pattern can be learned from spiral, radial, or other geometric pattern trajectories while allowing parameters that characterize the trajectories to be learned by the neural network.

In addition or alternatively, the actual k trajectories can be calculated based on a physical model that includes parameters for eddy current effects and/or concomitant gradient effect, and/or for Bo inhomogeneities. The neural network can receive prescan data (such as a Bo field map or pre-scan gradient delay measurements) as input. Together with the fully sampled baseline trajectories, an auto-correction for the k trajectories can be achieved. In one embodiment, the k trajectories are corrected by varying the gradient waveforms prior to the treatment scan. In addition or alternatively, the neural network used to correct k trajectories is integrated within the overall NNA.

In addition or alternatively, another physically driven loss function can be used, namely, the field map parameters that may be constructed from the echo images. In one embodiment, TMAP(ΔT), calculated based on Eq. (16), is used as the ground truth compared against the reconstructed, TMAP($\widehat{\Delta T}$) from the NNA. TMAP is the thermal map in real space obtained using the calculated ΔT at each pixel.

$$L_{\Delta T} = \|(TMAP(\widehat{\Delta T}, \overline{\theta}) - TMAP(\Delta T))\mu_2^2$$

In one embodiment, the UNet CNN architecture is employed. The $N_{coils}$ undersampled k-data can be used as the input data together with the $N_{coils}$ baseline k-data. In one embodiment, zero filling is set at the missing k-data points. In the case of non-Cartesian k sampling, gridding can be employed. Then the inverse Fourier transform of the k-data to real space is obtained. In one embodiment, the CNN is used iteratively where the loss function $L_{imag}$, is active within the CNN steps, but between CNN steps, data consistency loss terms, $L_{us}$, $L_{bl}$ are used. In another embodiment, an end-to-end CNN can proceed from k-space to the TMAP directly. Training data may be generated using a realistic and detailed Bloch simulations, which account for a wide variety of realistic features: phantom shape, magnetic field drift, RF interference, eddy currents, different temperature patterns, shape, size, scale, movements between baseline and treatment, and other features.

Another embodiment utilizes a generative adversarial network (GAN). In one embodiment, the generative network loss function is $L_{image}$ with L1 and or L2 regularization. The adversarial network may use data-consistency loss functions. Still another embodiment uses recurrent neural networks given the sequential nature of the treatment phases (including baseline phases).

Caffe, Keras, PyTorch, Theano and TensorFlow are suitable neural network platforms (and may be cloud-based or local to an implemented system in accordance with design preferences). For tasks involving images, CNNs are typically preferred as the major component in the NNA. The usage of CNN presented hereon is representative and actual implementation can use alternative networks as well and also combinations of NNAs. CNNs process images as input and may output a classification or another image, depending on design. For example, a CNN network based on the U-net architecture can be used to turn input data into an image. A CNN typically includes, inter alia, convolution layers and pooling layers that operate on the input image to produce an output.

More generally, embodiments of the present invention use a NNA to generate or identify a thermal map from an input k-space image with missing data with or without the addition of the full data that was collected as the base line k-data or multiple baselines. In one approach, a training library includes a series of k-space images with missing data and the full data of the baselines, and the labels are corresponding thermal maps. For example, the labels may be generated as described above from k-space images with missing data, which serve as the training input This approach utilizes a direct transform from the sub-sample k-space to the desired thermal maps. In another embodiment, the thermal map is created indirectly in two steps: the subsampled k space is first transformed into complex images (e.g., images from at least two echoes) using a NNA, and the resulting images are then used to generate thermal map using the conventional PRF technique. The first step of exploiting the NNA to reconstruct an MRI image from subsampled k-space may be accomplished using different techniques. In one approach, k-space is first completed (e.g., by assigning zeros to the missing data) and reconstructed to an image that will exhibit artifacts, which the CNN is used to remove. In another approach, the NNA generates the image directly from the subsampled k-space. Additionally, or alternatively, the NNA can be trained to accept as input at least one suboptimal thermal map (e.g., a map with artifacts) and generate as output one or more improved thermal maps (ML_Map). In some embodiments, the improved thermal maps can be used to further correct the reconstructed image (e.g., by replacing Eq. 11 with $F_1 = 2\pi K \Delta T = 2\pi K ML\_Map$).

Figure 7A:
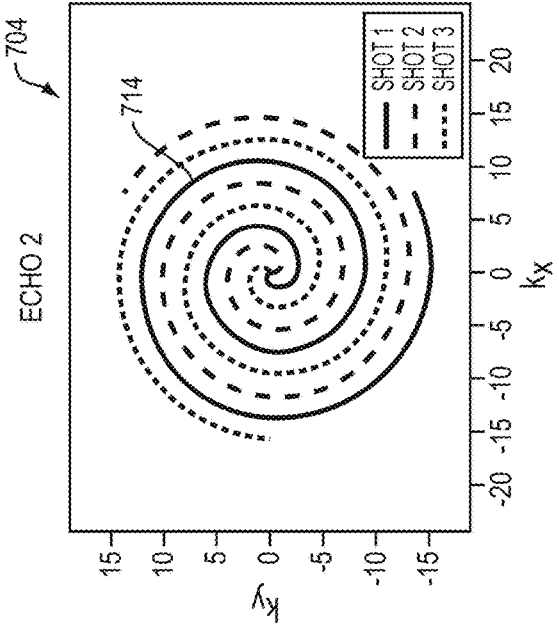
FIGS. 7A-7C illustrate how k-space data may be acquired in a spiral manner in accordance with various embodiments.
Figure 7B:
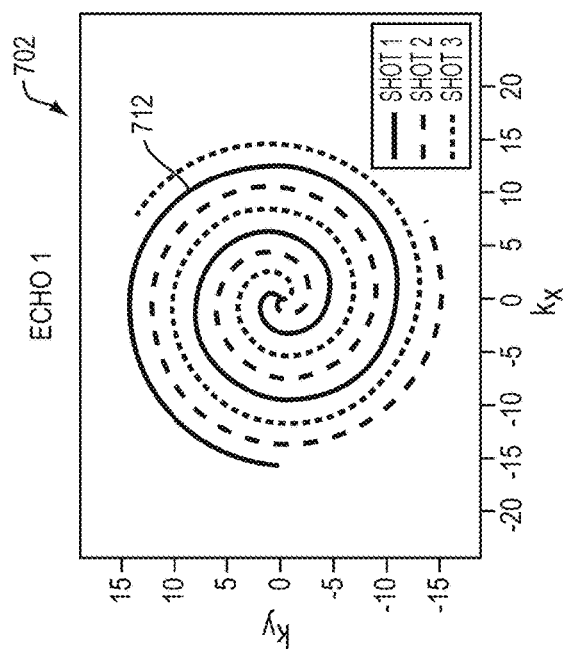
Figure 7C:
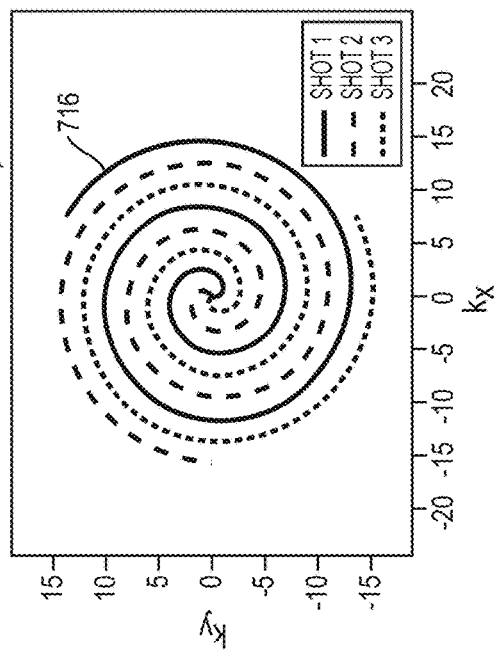

It should be noted that the MR accelerating approach described herein may be applied to any multi-echo MR pulse sequence; the under-sampled k-space data may be collected along any "incremented" dimensions (e.g., the phase-encoding dimension, spiral-interleaving dimension, radial-angle dimension, etc.) as long as the under-sampling is carried out in the echoes of the multi-echo trains. For example, the MR accelerating approach described herein may be applied in a multi-slice, multi-echo GRE pulse sequence and/or a multi-band, multi-echo GRE pulse sequence for acquiring 2D MR imaging slices, and the k-space trajectory may be Cartesian, spiral, radial or an arbitrary trajectory. For example, referring to FIGS. 7A-7C, the k-space data may be acquired in a spiral manner with three echoes 702-706 in each TR. In addition, each echo includes three shots but only one of them (e.g., the shots 712, 714, 716 in the echoes 702, 704, 706, respectively) is acquired; the other two shots are missing. Estimation of the missing data as described above may be applied to this scanning approach as well. For example, the missing shots may be computed numerically based on the constraints described above using the iterative estimation approach. Similarly, if the k-space data includes radial trajectories, under-sampling may be performed to reduce the number of "arms" in each echo. Subsequently, the iterative estimation approach together with the constraints may be implemented to determine the missing arms. Thus, while M scanning shots and N echoes (and thereby M×N total shots) are required in the conventional approaches to acquire an imaging slice, using the accelerated MR imaging approaches described herein may advantageously reduce the total number of shots by a factor or R (i.e., M×N/R). The same idea may be used in multi-shot multi-echo echo-planar imaging (EPI) for reducing the number of scanning shots as well.

In some embodiments, a volumetric 3D MR thermal map is desirable. In this situation, three dimensions of the k-space data may be acquired, and two of the dimensions (e.g., indirect Z-encoding, spiral interleaving, etc.) may be incremented. Accordingly, the data along any one or both two incremented dimensions may be under-sampled and estimated using the accelerated MR imaging approaches described above. For example, prior to treatment, the acquired k-space dataset(s) may include one or more full 3D baseline images. During treatment, the acquired k-space dataset(s) may include multiple shots corresponding to different values along the incremented dimension(s) in each TR; in addition, different shots may be sampled at different TEs. As a result, each shot in the treatment image may have some missing data. Again, because the main change between the baseline and treatment images is in the phase, the missing data in the treatment image(s) may be estimated using the iterative approach described above based on the constraint(s). In addition, the 3D data acquisition may be Cartesian acquisition, spiral acquisition, radial acquisition (see, e.g., https://onlinelibrary.wiley.com/doi/abs/10.1002/mrm.26862), a radial acquisition in combination with 2D spiral planes (see, e.g., https://www.ncbi.nlm.nih.gov/pubmed/28643383 and https://onlinelibrary.wiley.com/doi/abs/10.1002/mrm.26862) or an arbitrary trajectory. In one embodiment, the arbitrary trajectory is defined based on the acquired baseline.

Further, the methods for accelerating multi-echo GRE pulse sequences described herein are not limited to MR thermometry only. Other applications that use multi-echo GRE pulse sequences may also benefit from the accelerated MR data acquisition approaches. One example is the measurement of a field map, where fast field maps are acquired upon a field change or for construction of susceptibility-weighted imaging (SWI) using the multi-echo GRE pulse sequence. Another exemplary application is the study of $T_2^*$, where the magnitude contrast and signal decay per pixel between the echo images (e.g., micro-bleeding detection, BOLD PSD in f-MRI), as opposed to the phase, are under-sampled and estimated. Again, in all these applications, one or more fully sampled baseline images may be required prior to the procedures. If the baseline image(s) are not static with respect to the treatment image(s), a physical model may be integrated into the optimization procedure to predict and thereby compensate for the change (see, for example, Eq. (18)).

In some situations, the SNR of the acquired signals may be too low to provide meaningful estimation of the missing data using the constraints described above. For example, when detecting micro-bleeding of the brain tissue, local dark spots may appear along the echo train images (fast $T_2^*$); as a result, the linear relationship between TE and the phase difference at these spots cannot be measured due to low SNR. In one embodiment, a weighting mask can be applied to the pixels corresponding to the dark spots such that the unreliable constraints resulting therefrom do not influence the reconstructed images.

In addition, the MRI system may include multiple MRI coils; each coil may receive at least a portion of MR signals from the target region. Each of the k-space images acquired prior to and/or during the ultrasound procedure may be associated with one or more of the MRI coils. As a result, the reconstructed images may be based on the associated echo time as described above as well as the associated MRI coil(s). In one embodiment, information extracted from the MR signals received by the multiple coils may be merged; the merged information may be equivalent (or at least similar) to information measured using a single MR coil. Additionally or alternatively, the MR signals received by each coil may be processed as described above to reconstruct an image and/or generate a thermal map. The images and/or thermal maps associated with the multiple coils may then be collected, for example, using a weighted average to create an averaged image and/or thermal map of the target region.

In general, functionality for performing the accelerated MR imaging acquisition, including, under-sampling the k-space data and computationally determining the missing k-space data using the iterative estimation approach, as described above, whether integrated within a controller of the MRI system, and/or an ultrasound system, or provided by a separate external controller, may be structured in one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules. Finally, when there is a perturbation of the baseline magnitude, and a physical model is assumed (as described above), the optimization approach described above may include adjustment of the baseline images as well.

Certain embodiments of the present invention are described above. It is, however, expressly noted that the present invention is not limited to those embodiments; rather, additions and modifications to what is expressly described herein are also included within the scope of the invention.

What is claimed is:

1. An imaging system comprising:
   a magnetic resonance imaging (MM) apparatus configured to:
   (i) execute a first multi-echo pulse sequence to excite a target region;
   (ii) acquire a plurality of baseline k-space images of the target region, each baseline image being associated with an echo in the first multi-echo pulse sequence;
   (iii) execute a second multi-echo pulse sequence to excite the target region; and
   (iv) acquire a second plurality of k-space images, each of the second plurality of k-space images being associated with an echo in the second multi-echo pulse sequence and at least one of the second plurality of k-space images being under-sampled so as to be missing information compared to the baseline k-space images; and
   a computation unit configured to reconstruct a target image based at least in part on at least one baseline k-space image and at least one of the second plurality of k-space images.

2. The system of claim 1, wherein the target image is one of a thermal map, a susceptibility-weighted image, a $T_2^*$ image, a micro-bleeding image, or a BOLD f-MRI image.

3. The system of claim 1, wherein the computation unit comprises a neural network.

4. The system of claim 3, wherein the neural network is a convolutional neural network.

5. The system of claim 3, wherein the computation unit is configured to, for at least one of the second plurality of k-space images, (i) computationally estimate the information missing therefrom using the neural network, and (ii) generate a target image based at least in part on the estimated missing information.

6. The system of claim 3, wherein the computation unit is configured to, for at least one of the second plurality of k-space images, (i) computationally estimate a corresponding anatomical image using the neural network, and (ii) generate a target image based at least in part on the estimated anatomical image.

7. The system of claim 3, wherein the computation unit is configured to, for at least one of the second plurality of k-space images, (i) estimate the information missing therefrom and reconstruct a corresponding anatomical image, (ii) computationally correct the anatomical image using the neural network, and (ii) generate a target image based at least in part on the corrected anatomical image.

8. The system of claim 1, wherein the computation unit is configured to, for at least one of the second plurality of k-space images, (i) computationally estimate the information missing therefrom, (ii) computationally update the estimated missing information based at least in part on an echo time associated therewith, and (iii) generate a map based at least in part on the updated estimated missing information, the at least one of the second plurality of k-space images corresponding thereto, and the baseline k-space image corresponding to the at least one of the second plurality of k-space images.

9. The system of claim 8, wherein the map comprises at least one of an anatomical image or a thermal map of the target region.

10. The system of claim 8, wherein the computation unit is further configured to computationally estimate the missing information based at least in part on a default value, a portion of one of the corresponding baseline k-space images, or a different one of the second plurality of k-space images.

11. The system of claim 8, wherein each one of the baseline k-space images comprises a plurality of pixels, the computation unit being further configured to update the estimated missing information based at least in part on a magnitude associated with a pixel in one of the baseline k-space images.

12. The system of claim 1, further comprising a first and a second MRI coil, wherein each of the baseline k-space images and each of the second plurality of k-space images is associated with at least one of the first or second MRI coil.

13. The system of claim 8, wherein the computation unit is further configured to (a) computationally reconstruct a plurality of baseline images from the plurality of baseline k-space images, and (b) for each one of the second plurality of k-space images, computationally reconstruct an image in a third image set based at least in part on the computationally estimated missing information associated therewith.

14. The system of claim 13, wherein each one of the baseline k-space images is acquired from an echo in response to the first multi-echo pulse sequence and each one of the second plurality of k-space images is acquired from an echo in response to the second multi-echo pulse sequence, the computation unit being further configured to correspond each reconstructed image in the third image set to one of the reconstructed baseline images based at least in part on echo times of the echoes associated therewith.

15. The system of claim 14, further comprising a plurality of MRI coils, each of the baseline k-space images and each of the second plurality of k-space images being associated with at least one of the MM coils, the computation unit being further configured to relate each reconstructed image in the third image set to one of the reconstructed baseline images based at least in part on the associated at least one MRI coil.

16. The system of claim 14, wherein the echo time associated with the reconstructed image in the third image set is the same as the echo time associated with the corresponding reconstructed baseline image.

17. The system of claim 14, wherein the computation unit is further configured to (c) determine a phase difference between a pixel in one of the reconstructed baseline images and the corresponding pixel in the corresponding reconstructed image in the third image set.

18. The system of claim 17, wherein the computation unit is further configured to (d) update the phase difference based at least in part on the echo time of the k-space image from which said corresponding reconstructed image in the third image set is reconstructed.

19. The system of claim 18, wherein the phase differences associated with the reconstructed images in the third image set positively correlate with the echo times of the second plurality of k-space images.

20. The system of claim 18, wherein the computation unit is further configured to update the phase difference based at least in part on the echo times associated with at least two different images in the second plurality of k-space images.

21. The system of claim 18, wherein the computation unit is further configured to (e) update said corresponding reconstructed image in the third image set based at least in part on the updated phase difference, and (f) transform the updated image to a k-space image in a fourth image set.

22. The system of claim 17, wherein the computation unit is further configured to (g) update the k-space image in the fourth image set based at least in part on the corresponding image in the second plurality of k-space images acquired at a same echo time.

23. The system of claim 22, wherein the computation unit is further configured to iteratively perform steps (b)-(g) until a termination condition is satisfied.

24. The system of claim 23, wherein the termination condition corresponds to one or more of:
  a number of iterations exceeding a predetermined limit, or
  a change in the updated k-space image in the fourth image set or in the reconstructed image in the third image set between two iterations being below a predetermined minimum.

25. The system of claim 22, wherein the computation unit is further configured to execute an artificial neural network for performing steps (b)-(g) at least two times.

26. The system of claim 22, wherein the computation unit is further configured to computationally reconstruct an image in a fifth image set based at least in part on the updated k-space image in the fourth image set and computationally reduce noise from the reconstructed image in the fifth image set.

27. The system of claim 26, wherein the computation unit is further configured to apply a locally low-rank regularization to at least two of the images in at least one of the third image set or the fifth image set for reducing the noise therein.

28. A method of magnetic resonance imaging, the method comprising:
  causing a magnetic resonance imaging (MRI) apparatus to perform the steps of:
    executing a first multi-echo pulse sequence to excite a target region;
    acquiring a plurality of baseline k-space images of the target region, each baseline image being associated with an echo in the first multi-echo pulse sequence;
    executing a second multi-echo pulse sequence to excite the target region;
    acquiring a second plurality of k-space images, each of the second plurality of k-space images being associated with an echo in the second multi-echo pulse sequence and at least one of the second plurality of k-space images being under-sampled so as to be missing information compared to the baseline k-space images; and
  causing a computation unit to perform the step of reconstructing a target image based at least in part on at least one baseline k-space image and at least one of the second plurality of k-space images.

* * * * *